United States Patent
Monteil et al.

(10) Patent No.: US 11,267,482 B2
(45) Date of Patent: Mar. 8, 2022

(54) MITIGATING RISK BEHAVIORS

(71) Applicant: International Business Machines Corporation, Armonk, NY (US)

(72) Inventors: Julien Monteil, Dublin (IE); Yassine Lassoued, Dublin (IE); Sergio Cabrero Barros, Dublin (IE); Rodrigo Hernan Ordonez-Hurtado, Maynooth (IE); Martin Mevissen, Dublin (IE); Sergiy Zhuk, Dublin (IE); Nigel Hinds, Great Barrington, MA (US); Bo Wen, New York, NY (US); Jeffrey Rogers, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 383 days.

(21) Appl. No.: 16/599,188

(22) Filed: Oct. 11, 2019

(65) Prior Publication Data
US 2021/0107501 A1   Apr. 15, 2021

(51) Int. Cl.
*G01M 17/00*   (2006.01)
*B60W 50/08*   (2020.01)
(Continued)

(52) U.S. Cl.
CPC ........... *B60W 50/087* (2013.01); *A61B 3/165* (2013.01); *A61B 5/01* (2013.01); *A61B 5/02055* (2013.01);
(Continued)

(58) Field of Classification Search
CPC ..... B60W 50/087; B60W 40/09; A61B 5/163; A61B 5/369; A61B 5/389; A61B 3/165;
(Continued)

(56) References Cited

U.S. PATENT DOCUMENTS 6,809,643 B1   10/2004   Elrod
8,725,311 B1    5/2014   Breed
(Continued)

FOREIGN PATENT DOCUMENTS

WO   2003070093 A1   8/2003
WO   2013113947 A1   10/2014
(Continued)

OTHER PUBLICATIONS

Lanata et al., "How the Autonomic Nervous System and Driving Style Change With Incremental Stressing Conditions During Simulated Driving", IEEE Transactions on Intelligent Transportation Systems, 1524-9050 © 2014 IEEE, 13 pages.
(Continued)

*Primary Examiner* — Adam M Alharbi
(74) *Attorney, Agent, or Firm* — Randy E. Tejeda

(57) ABSTRACT

In an approach to predicting physiological and behavioral states utilizing models representing relationships between driver health states and vehicle dynamics data, one or more computer processors capture one or more vehicle motion parameters. The one or more computer processors to capture one or more physiological parameters; identify contextual data associated with the one or more captured vehicle motion parameters and the one or more captured physiological parameters; predict one or more driving behavior parameters by utilizing one or more physical models fed with the one or more vehicle motion parameters and the identified contextual data; predict one or more driver health parameters by utilizing a model trained with the one or more captured physiological parameters and the identified contextual data; generate a risk assessment based on the one or more predicted driving behavior parameters and the one or more predicted driver health parameters.

20 Claims, 5 Drawing Sheets

(51) Int. Cl.
  *G06N 5/02*    (2006.01)
  *B60W 40/09*   (2012.01)
  *G06Q 40/08*   (2012.01)
  *A61B 5/0205*  (2006.01)
  *A61B 5/01*    (2006.01)
  *A61B 3/16*    (2006.01)
  *A61B 5/16*    (2006.01)
  *A61B 5/145*   (2006.01)
  *A61B 5/18*    (2006.01)
  *A61B 5/00*    (2006.01)
  *G06N 20/00*   (2019.01)
  *A61B 5/369*   (2021.01)
  *A61B 5/389*   (2021.01)
  *A61B 5/08*    (2006.01)
  *A61B 5/0533*  (2021.01)
  *A61B 5/024*   (2006.01)
  *A61B 5/021*   (2006.01)

(52) U.S. Cl.
  CPC .......... *A61B 5/14532* (2013.01); *A61B 5/163* (2017.08); *A61B 5/18* (2013.01); *A61B 5/369* (2021.01); *A61B 5/389* (2021.01); *A61B 5/6893* (2013.01); *A61B 5/7275* (2013.01); *B60W 40/09* (2013.01); *G06N 5/02* (2013.01); *G06N 20/00* (2019.01); *G06Q 40/08* (2013.01); *A61B 5/021* (2013.01); *A61B 5/024* (2013.01); *A61B 5/0533* (2013.01); *A61B 5/0816* (2013.01); *B60W 2520/10* (2013.01); *B60W 2520/105* (2013.01); *B60W 2520/14* (2013.01); *B60W 2520/16* (2013.01); *B60W 2520/18* (2013.01); *B60W 2530/10* (2013.01); *B60W 2540/22* (2013.01); *B60W 2540/30* (2013.01); *B60W 2552/00* (2020.02); *B60W 2554/801* (2020.02); *B60W 2555/20* (2020.02); *B60W 2555/60* (2020.02)

(58) Field of Classification Search
  CPC ... A61B 5/01; A61B 5/02055; A61B 5/14532; A61B 5/18; A61B 5/6893; A61B 5/7275; G06N 20/00; G06N 5/02; G06Q 40/08
  See application file for complete search history.

(56) References Cited

U.S. PATENT DOCUMENTS

| | | |
|---|---|---|
| 8,874,301 B1 | 10/2014 | Rao |
| 2015/0186714 A1* | 7/2015 | Ren ............ H04N 7/183 348/77 |
| 2015/0302718 A1 | 10/2015 | Konigsberg |
| 2016/0086393 A1* | 3/2016 | Collins ............ G07C 5/0808 701/31.5 |
| 2018/0082496 A1* | 3/2018 | Rosenbaum ........ G06Q 40/08 |
| 2019/0102689 A1 | 4/2019 | Lassoued |

FOREIGN PATENT DOCUMENTS

| | | |
|---|---|---|
| WO | 2016028228 A1 | 2/2016 |
| WO | 2019069732 A1 | 4/2019 |

OTHER PUBLICATIONS

Paredes et al., "Fast & Furious: Detecting Stress with a Car Steering Wheel", CHI 2018, Apr. 21-26, 2018, Montreal, QC, Canada, © 2018 ACM. ISBN 978-1-4503-5620—Jun. 18, 2004, 12 pages.

* cited by examiner

MITIGATING RISK BEHAVIORS

BACKGROUND

The present invention relates generally to the field of transportation safety, and more particularly to mitigating risk behaviors based on relationships between physiological and behavioral states.

Modern road safety makes a distinction between the situation and the management systems necessary to control it, with prevention activities that largely exceed the fields of the traditional 3E (Engineering, Enforcement, Education) approach. Modern Management systems have the aims of being inclusive, i.e. to include explicitly all activities part of a system forming an integrated whole. Active safety is increasingly being used to describe systems that use an understanding of the state of the vehicle to both avoid and minimize the effects of an incident. Active systems include braking systems, like brake assist, traction control systems and electronic stability control systems, that interpret signals from various sensors to help the driver control the vehicle. Additionally, sensor-based systems such as advanced driver-assistance systems including adaptive cruise control and collision warning, avoidance, and mitigation systems are also considered as active safety systems under this definition. Active safety systems are systems activated in response to a safety problem or abnormal event. Such systems may be activated by a human operator, automatically by a computer driven system, or even mechanically. In the automotive sector the term active safety (or primary safety) refers to safety systems that are active prior to an accident. Said safety systems contain highly advanced systems such as anti-lock braking system, electronic stability control and collision warning/avoidance through automatic braking, distinguishable with passive safety (or secondary safety), which are active during an accident.

SUMMARY

Embodiments of the present invention disclose a computer-implemented method, a computer program product, and a system for predicting physiological and behavioral states utilizing models representing relationships between driver health states and vehicle dynamics data. The computer-implemented method includes one or more computer processors capturing one or more vehicle motion parameters. The one or more computer processors to capture one or more physiological parameters. The one or more computer processors identify contextual data associated with the one or more captured vehicle motion parameters and the one or more captured physiological parameters. The one or more computer processors predict one or more driving behavior parameters by utilizing one or more physical models fed with the one or more vehicle motion parameters and the identified contextual data. The one or more computer processors predict one or more driver health parameters by utilizing a model trained with the one or more captured physiological parameters and the identified contextual data. The one or more computer processors to generate a risk assessment based on the one or more predicted driving behavior parameters and the one or more predicted driver health parameters.

DETAILED DESCRIPTION

Traditional systems and methods monitor a health state of a driver utilizing health devices for a variety of purposes. Some systems and methods focus on detecting and mitigating risk associated with certain states (e.g., fatigue, sleepiness, distraction, stress). Other systems and methods aim to adapt or adjust vehicle settings to optimize the comfort of a driver (e.g., adjusting seat to reduce back pain). The aforementioned traditional systems do not account nor incorporate real effects of a physiological state of a driver on one or more aspects of driving. Furthermore, said systems do not accurately judge or evaluate the risk associated with a health state of a driver.

Embodiments of the present invention address traditional limitations by learning the relationship between health states (e.g., driver health) and driving behavior parameters of a driver. Embodiments of the present invention allow for an accurate understanding (e.g., prediction) of driving outcomes (e.g., predictors) due to physiological states providing a mechanism for inferring or estimating the driving behavior parameters from physiological data, associated health states, and vehicle dynamics. Some embodiments of the present invention recognize that accurately and effectively assessing and mitigating driver risk reduces, limits, or eliminates the cost and toll of preventable vehicle incidents, accidents, and collisions. Embodiments of the present invention combine physiological readings and vehicle dynamics data to accurately access some measure of risk. Embodiments of the present invention recognize that vehicle dynamics data can be used as a proxy for the health state and physiological data can be used as a proxy for driving behavior, based on contextual data. Embodiments of the present invention utilize one or more generated risk assessments to control one or more autonomous vehicle, allowing the system to control said vehicles to prevent vehicle incidents, accidents, and collisions. Embodiments of the present invention recognize that system efficiency is improved by correlating low order parameters (e.g., vehicle dynamics and physiological readings) to higher order parameters (e.g., behavioral parameters), allowing a system to save considerable system resources by removing lower order parameters after processing while retaining lower order significance. Implementation of embodiments of the invention may take a variety of forms, and exemplary implementation details are discussed subsequently with reference to the Figures.

The present invention will now be described in detail with reference to the Figures.

Figure 1:
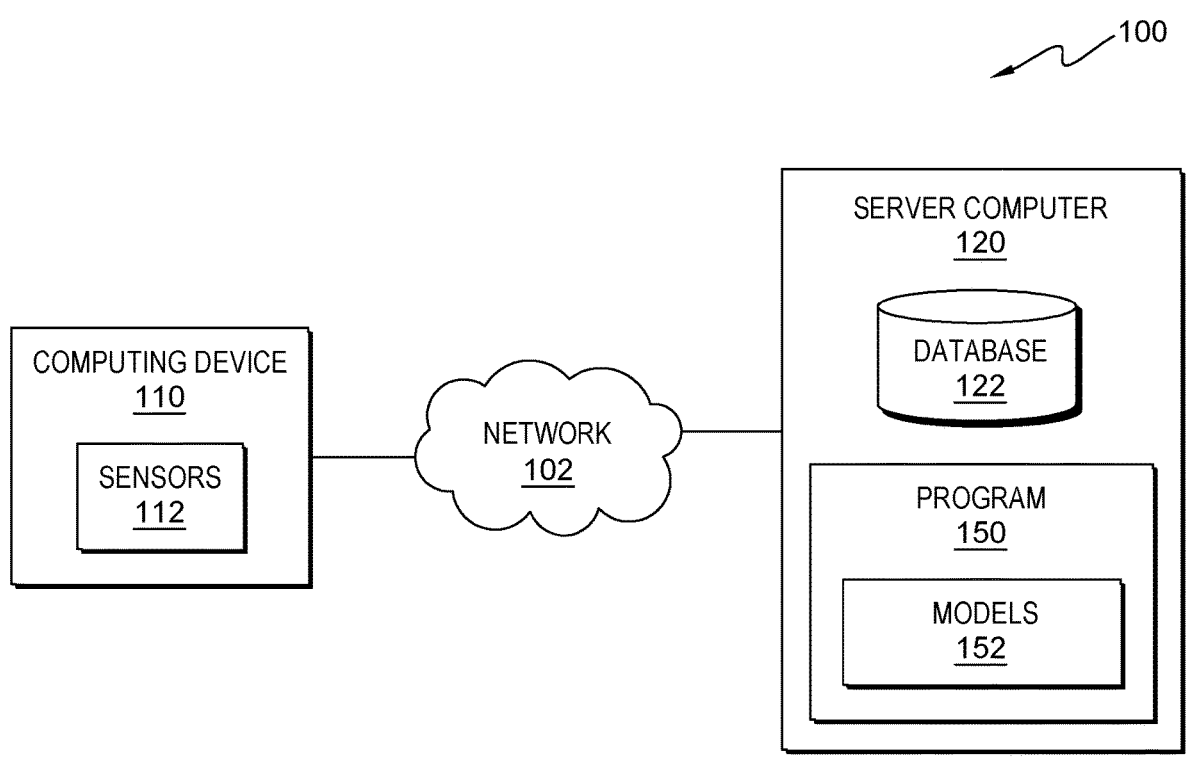
FIG. 1 is a functional block diagram illustrating a distributed data processing environment, in accordance with an embodiment of the present invention.

FIG. 1 is a functional block diagram illustrating a distributed data processing environment, generally designated 100, in accordance with one embodiment of the present invention. The term "distributed" as used in this specification describes a computer system that includes multiple, physically, distinct devices that operate together as a single computer system. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes computing device 110 and server computer 120, interconnected over network 102. Network 102 can be, for example, a telecommunications network, a local area network (LAN), a wide area network (WAN), such as the Internet, or a combination of the three, and can include wired, wireless, or fiber optic connections. Network 102 can include one or more wired and/or wireless networks that are capable of receiving and transmitting data, voice, and/or video signals, including multimedia signals that include voice, data, and video information. In general, network 102 can be any combination of connections and protocols that will support communications between computing device 110, server computer 120, and other computing devices (not shown) within distributed data processing environment 100. In various embodiments, network 102 operates locally via wired, wireless, or optical connections and can be any combination of connections and protocols (e.g., personal area network (PAN), near field communication (NFC), laser, infrared, ultrasonic, etc.).

Computing device 110 may be any electronic device or computing system capable of processing program instructions and receiving and sending data. In some embodiments, computing device 110 may be a laptop computer, a tablet computer, a netbook computer, a personal computer (PC), a desktop computer, a personal digital assistant (PDA), a smart phone, or any programmable electronic device capable of communicating with network 102. In other embodiments, computing device 110 may represent a server computing system utilizing multiple computers as a server system, such as in a cloud computing environment.

In various embodiments, computing device 110 is a smart phone. Smart phones may be used as a biometric sensor, telephone, digital camera, video camera, global positing system (GPS) navigation, a media player, clock, news, calculator, web browser, handheld video game player, flashlight, compass, an address book, note-taking, digital messaging, an event calendar, etc. In another embodiment, computing device 110 may each be a wearable computer such as a smartwatch or a fitness tracker. Wearable computers are miniature electronic devices that may be worn by the bearer under, with, or on top of clothing, as well as in or connected to glasses, hats, or other accessories. Fitness trackers are devices or applications for monitoring and tracking fitness-related metrics such as user speed, acceleration, change in direction, distance traveled, calorie consumption, and biometric data such as heart and perspiration rates. In some embodiments, computing device 110 is an onboard computer and associated sensors of an automobile (not shown) that are capable of communicating with server computer 120 over network 102. In other embodiments, the automobile may have multiple computing devices that each make up computing device 110, where one or more of the multiple computing devices include user interfaces (not shown). In an example, computing device 110 is a vehicle with a touch screen that enables the user to view and manipulate objects and controls based on user (i.e., driver) input. In general, computing device 110 is representative of any electronic device or combination of electronic devices capable of executing machine readable program instructions as described in greater detail with regard to FIG. 4, in accordance with embodiments of the present invention. In the depicted embodiment, computing device 110 contains sensors 112.

Sensors 112 contains a plurality of sensors utilized by program 150. In an embodiment, sensors 112 contains plurality of biometric sensors capable of monitoring, detecting, storing, and transmitting a plurality of physiological parameters and data such as heartrate, electrodermal response, etc. For example, a user utilizes a fitness tracker to monitor, track, and store heart rate and metabolic statistics. In various embodiments, sensors 112 may include, but not limited to, fitness trackers, biofeedback devices, and any device capable of sensing and reporting a plurality of physiological parameters and data. In an example, a biofeedback device may measure electromyography (EMG), muscle tension as it changes over time; thermal or temperature, body temperature changes over time; electroencephalography, brain wave activity over time; galvanic skin response, amount of sweat on your body over time; and heart variability biofeedback, pulse and heart rate. In an embodiment, sensors 112 may include facial and body image recognition that can infer physiological parameters and data from facial expressions, body posture, and associated facial/body landmarks. For example, sensors 112 identifies a significant hypertension event in a driver by recognizing the tension of specific muscles in the face of the driver.

In an embodiment, sensors 112 is a plurality of devices or sensors that are capable of measuring acceleration. In various embodiments, sensors 112 are solid-state accelerometers based on microelectromechanical systems (MEMS). In various embodiments, accelerometers, contained within sensors 112, are able to detect the magnitude and the direction of acceleration/deacceleration, as well as orientation, coordinate acceleration, vibration, and shock of a vehicle. In an example, sensors 112 is capable determining motions changes in 6-axis: X (forward/back, surge), Y (left/right, sway), Z (up/down, heave), yaw, pitch, and roll. In an example, sensors 112 may measure sway, roll, and yaw during a cornering maneuver. In the depicted embodiment, sensors 112 is located within computing device 110, however sensors 112 may also be located within any number of computing devices known in the art such as a fitness trackers, smartwatches, and on-board diagnostic (ODB) devices. In another embodiment, sensors 112 include facial recognition systems, temperature sensors, radar, lidar, sonar, wheel position sensor (WPS), a plurality of cameras (e.g., front-facing, rear-facing, surround systems, night vision, etc.), wireless positioning systems, infrared lasers, and single-photon avalanche diodes (SPAD).

In another embodiment, sensors 112 contains a global positioning sensor (GPS). In this embodiment, sensors 112 is a device, receiver, or sensor that is capable of receiving information from GPS satellites and calculating the device's geographical position. In most embodiments, said GPS utilizes a track algorithm that combines sets of satellite measurements collected at different times. After a set of measurements are processed, the track algorithm predicts the receiver location corresponding to the next set of satellite measurements. When the new measurements are collected, the receiver uses a weighting scheme to combine the new measurements with the tracker prediction. In general, a tracker can (a) improve receiver position and time accuracy, (b) reject bad measurements, and (c) estimate receiver speed and direction. Sensors 112 also detects and derives (e.g., predicts) information regarding orientation and speed.

Server computer 120 can be a standalone computing device, a management server, a web server, a mobile computing device, or any other electronic device or computing system capable of receiving, sending, and processing data. In other embodiments, server computer 120 can represent a server computing system utilizing multiple computers as a server system, such as in a cloud computing environment. In another embodiment, server computer 120 can be a laptop computer, a tablet computer, a netbook computer, a personal computer (PC), a desktop computer, a personal digital assistant (PDA), a smart phone, or any programmable electronic device capable of communicating with computing device 110 and other computing devices (not shown) within distributed data processing environment 100 via network 102. In another embodiment, server computer 120 represents a computing system utilizing clustered computers and components (e.g., database server computers, application server computers, etc.) that act as a single pool of seamless resources when accessed within distributed data processing environment 100. In the depicted embodiment, server computer 120 includes database 122 and program 150. In other embodiments, server computer 120 may contain other applications, databases, programs, etc. which have not been depicted in distributed data processing environment 100. Server computer 120 may include internal and external hardware components, as depicted and described in further detail with respect to FIG. 4.

Database 122 (e.g., behavioral and health parameter database) is a repository for data used by program 150. In the depicted embodiment, database 122 resides on server computer 120. In another embodiment, database 122 may reside on computing device 110 or elsewhere within distributed data processing environment 100 provided program 150 has access to database 122. A database is an organized collection of data. Database 122 can be implemented with any type of storage device capable of storing data and configuration files that can be accessed and utilized by program 150, such as a database server, a hard disk drive, or a flash memory. In an embodiment, database 122 stores data used by program 150, such as physiological data and vehicle dynamics data. In various embodiments, physiological data contains any measurement of health of a driver including (e.g., group, selection, etc.), but is not limited to, electrodermal response, glucose levels, breathing rate, heart rate, electromyography (EMG) feedback, electroencephalography feedback, galvanic skin response, blood pressure, pupil dilation, eye pressure, and body temperature. In an embodiment, physiological data includes associated health states (e.g., driver health) such as stress, attention, fatigue, sleepiness, distraction, etc. Physiological data can be captured, monitored, derived, logged and stored from a plurality of sensors included within sensors 112 (e.g., heart monitor, glucose monitor, facial landmark recognition, etc.), as detailed in the description of sensors 112.

In an embodiment, vehicle dynamics data, how a vehicle behaves in motion, contains any measurement (e.g., vehicle motion parameters) of a vehicle, including (e.g., group), but not limited to, speed, acceleration, longitudinal and lateral distances to surrounding vehicles, orientation, coordinate acceleration, noise, vibration, shock, wobble, weight transfer, load transfer, yaw, roll, pitch, body roll, bump steer, body flex, etc. In various embodiments, vehicle dynamics data is associated (e.g., linked, paired, joined, referenced, etc.) with contextual data such as weather, traffic status, road quality, speed limits, special considerations (e.g., construction, natural disasters, regional events), etc. For example, for a specified time step of vehicle dynamics data, program 150 identifies and joins contextual data (e.g., weather conditions during the time step) related to the time step. In another embodiment, program 150 associates (e.g., links) contextual data with captured health state parameters and calculated physiological parameters and data. In various embodiments, database 122 contains stored, inferred, or derived drive behavior parameters such as aggressiveness, average reaction time, smoothness (e.g., g-forces, turn radius, etc.). In an embodiment, database 122 contains historical (e.g., captured, predicted, or calculated) vehicle dynamics data and physiological data, such as vehicle parameters driver parameters, past trips, offenses, incidents (e.g., accidents, errors, etc.), and associated actions (e.g., remedial, corrective, informative, etc.). In various embodiments, program 150 creates and maintains a plurality of training sets that include subsets of a plurality of features representative of the information, data, and parameters described above.

Database 122 may also store one or more user parameters associated with default or pre-defined values including, but not limited to, maximum driver speed, maximum driver acceleration and/or maximum braking force. In an embodiment, database 122 contains rules for each data type or parameter, which include a condition-action pair. For example, if a glucose level of a driver falls to a certain level (e.g., condition), then program 150 may infer a physiological condition (hypoglycemic) or a health state (e.g., inattentiveness, etc.) In another embodiment, database 122 may be a geographic information system (GIS) database.

Models 152 contains a plurality of models (e.g., learners, estimators, assessors, predictors, etc.) such as physical models, physiological-behavioral models, physiological-behavioral mapping models, risk assessors, behavioral parameter learners (e.g., estimates behavioral parameters using physical models and input data), etc. In an embodiment, models 152 is a sub-module or agent of program 150. In an embodiment, physical models characterize longitudinal and lateral behavior of a driver based on the vehicle speed, relative positioning, relative speeds of surrounding vehicles. In this embodiment, program 150 utilizes a physical model as an intermediate step to track the evolution (time series) of behavioral parameters. In an embodiment, program 150 utilizes the physical model illustrated in FIG. 3B. Program 150 utilizes the outputs of the aforementioned physical models to calculate behavioral parameters that define a plurality of behavioral conditions of the driver and, in turn, can derive (e.g., predict) risk (e.g., a short reaction time is safe, a high lane changes aggressiveness is unsafe, a higher than usual reaction time denotes a fatigue condition, a higher than usual lane change aggressiveness denotes stress, etc.). For example, program 150 may utilize the following physical model to determine behavioral parameters:

$$\ddot{x}_n(t+\tau) = \alpha \cdot (\dot{x}_{n+1}(t) - \dot{x}_n(t)) \tag{1}$$

With respect to equation (1), $\tau$ is reaction time and $\alpha$ is aggressiveness.

In various embodiments, physiological-behavioral models and physiological-behavioral mapping models learn the correlation between behavioral and physiological parameters, infer the physiological parameters from behavioral parameters, and predict behavioral parameters based on physiological parameters. Physiological-behavioral models and physiological-behavioral mapping models may utilize machine learning models and algorithms to predict learn, infer, and predict. In an embodiment, said models contain a plurality of transferrable neural networks algorithms and models (e.g., long short-term memory (LSTM), deep stacking network (DSN), deep belief network (DBN), convolutional neural networks (CNN), compound hierarchical deep models, etc.) that can be trained with supervised and/or unsupervised methods. In a further embodiment, models 152 contains physiological-behavioral models and physiological-behavioral mapping models utilizes recurrent neural networks (RNNs) trained utilizing supervised training methods. In various embodiments, physiological data is labeled with an expected output (e.g., health states and behavioral parameters) enabling models 152 the ability to learn what features are correlated to a health state or behavioral parameter.

Models 126 may contain a plurality of risk assessors that compare learned behavioral/physiological parameters to individual or collective distributions of behavioral/physiological parameters for a given context (e.g., contextual data associated with timesteps) and assess a driving risk. Risk assessors may consider one or more operating conditions (e.g., driving parameters, physiological data, associated data, etc.) of a driver/vehicle and generate a risk assessment (e.g., score, value, rating, etc.) by considering different features, available as structured or unstructured data, and applying relative numerical weights. Risk assessors can generate risk assessments based on continuous data aggregated and fed by program 150. In an embodiment, risk assessors learn from the training set of data to distinguish between risky and not risky parameters. In an embodiment, program 150 trains one or more risk assessors utilizing historically predicted driving behavior parameters and one or more historically predicted driver health parameters. In a further embodiment, program 150 trains one or more risk assessors with additional parameters such as historically capture vehicle motion parameters and historically captured physiological parameters. The training and utilization of the models contained in models 152 is depicted and described in further detail with respect to FIG. 2.

Program 150 is a program for predicting physiological and behavioral states utilizing models representing relationships between driver health states and vehicle dynamics data. In the depicted embodiment, program 150 is a standalone software program. In another embodiment, the functionality of program 150, or any combination programs thereof, may be integrated into a single software program. In some embodiments, program 150 may be located on separate computing devices (not depicted) but can still communicate over network 102. In various embodiments, client versions of program 150 resides on computing device 110 and/or any other computing device (not depicted) within distributed data processing environment 100. In the depicted embodiment, program 150 contains models 152. Program 150 is depicted and described in further detail with respect to FIG. 2.

The present invention may contain various accessible data sources, such as database 122, that may include personal storage devices, data, content, or information the user wishes not to be processed. Processing refers to any, automated or unautomated, operation or set of operations such as collection, recording, organization, structuring, storage, adaptation, alteration, retrieval, consultation, use, disclosure by transmission, dissemination, or otherwise making available, combination, restriction, erasure, or destruction performed on personal data. Program 150 provides informed consent, with notice of the collection of personal data, allowing the user to opt in or opt out of processing and collection of personal data. Consent can take several forms. Opt-in consent can impose on the user to take an affirmative action before the personal data is processed. Alternatively, opt-out consent can impose on the user to take an affirmative action to prevent the processing of personal data before the data is processed. Program 150 enables the authorized and secure processing of user information, such as tracking information, as well as personal data, such as personally identifying information or sensitive personal information. Program 150 provides information regarding the personal data and the nature (e.g., type, scope, purpose, duration, etc.) of the processing. Program 150 provides the user with copies of stored personal data. Program 150 allows the correction or completion of incorrect or incomplete personal data. Program 150 allows the immediate deletion of personal data.

In various embodiments, the term "vehicle" should be construed having a broad meaning and should include all types of vehicles. Non-limiting examples of vehicles include passenger cars, trucks, motorcycles, off-road/all-terrain vehicles, buses, boats, airplanes, helicopters, recreational vehicles, farm vehicles, construction vehicles, trams, golf carts, vehicle platoons, trains, and/or trolleys. In various embodiments, the term "drive" should be construed having a board meaning and should include operating all types of vehicles as delineated above.

In various embodiments, the term "user" or "driver" should be construed having a broad meaning and should include all types of entities managing or operating a vehicle. Non-limiting examples of users and drivers include human drivers, automated driving systems (e.g., lead vehicle in a platoon of vehicles), semi-automated driving systems, and remote driving systems.

Figure 2:
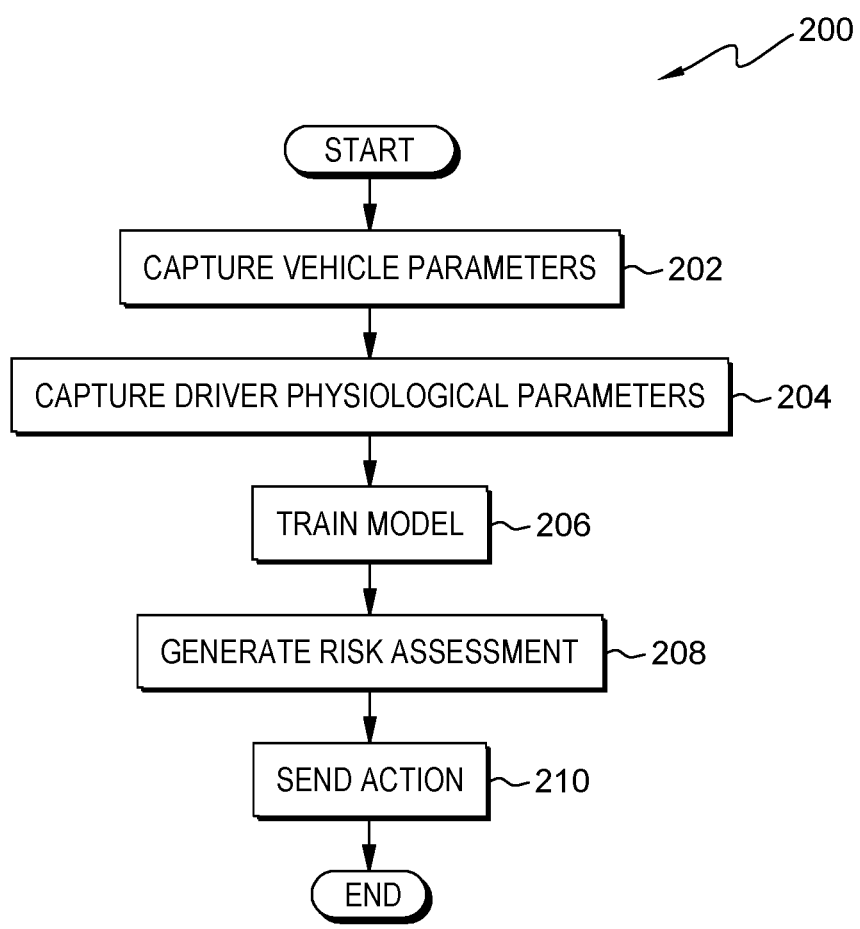
FIG. 2 is a flowchart depicting operational steps of a program, on a server computer within the data processing environment of FIG. 1, for predicting physiological and behavioral states utilizing models representing relationships between driver health states and vehicle dynamics data, in accordance with an embodiment of the present invention.

FIG. 2 is a flowchart depicting operational steps of program 150 for predicting physiological and behavioral states utilizing models representing relationships between driver health states and vehicle dynamics data, in accordance with an embodiment of the present invention.

Program 150 captures vehicle dynamics parameters (step 202). Program 150 is initiated to continuously monitor one or more vehicle sensors or devices within a vehicle to capture, store, and transmit one or more vehicle dynamics parameters. In an embodiment, program 150 receives a notification a user has entered a vehicle, then initiates. For example, program 150 receives a notification from a smart device of a user (e.g., computing device 110) if the user is moving faster than normal walking speed. In another embodiment, program 150 may receive a prompt from a user to initiate program 150. In an embodiment, when a user of a computing device 110 enters wireless communication range with a vehicle, program 150 identifies the user and the vehicle.

Program 150 records vehicle dynamics data, containing any measurement of vehicle dynamics, including, but not limited to, speed, acceleration, longitudinal and lateral distances to surrounding vehicles, orientation, coordinate acceleration, vibration, shock, etc. In an embodiment, program 150 utilizes the ODB port of the vehicle to measure vehicle dynamics. In this embodiment, the data from the ODB port can provide additional parameters and/or provide more accurate measurements than are possible with general-purpose devices such as a smartphone. In various embodiments, program 150 utilizes a plurality of sensors contained within sensors 112 to detect one or more changes to vehicle dynamics such as the direction of acceleration and acceleration, orientation, coordinate acceleration, vibration, and shock. In an example, program 150 records vehicle motion changes in 6-axis: X (forward/back, surge), Y (left/right, sway), Z (up/down, heave), yaw, pitch, and roll. In an example, sensors 112 may measure sway, roll, and yaw during a vehicle cornering maneuver. In various embodiments, program 150 utilizes radar, lidar, sonar, a plurality of cameras (e.g., front-facing, rear-facing, surround systems, night vision, etc.), infrared lasers, single-photon avalanche diodes (SPAD) to detect, measure, and record the location and distances between the vehicle of the user and other vehicles in proximity with the vehicle of the user. In another embodiment, program 150 may utilize ultrasonic sensors (e.g., parking sensors, blind spot sensors, etc.), radar, and lidar to detect nearby vehicles and derive following distance parameters. For example, program 150 records that a vehicle has been following another vehicle at an average distance of 15 feet.

In a further embodiment, program 150 utilizes GPS, contained within sensors 112, to measure driving metrics along with geographical data. For example, program 150 may utilize said GPS to derive the average speed of a vehicle on highways. In other embodiments, program 150 may utilize computing device (e.g., mobile phone, etc.) tracking, via triangulation of radio signals between cell towers. In another embodiment, program 150 may utilize video/image recognition to determine the location of the user. For example, as a user travels, program 150 determines the location of the user by analyzing the video stream from a front facing dashcam to identify street names, buildings, or landmarks. Program 150 utilizes GPS and a plurality of news and weather applications (not depicted) to provide contextual information, parameters, and data in relation to one or more record vehicle dynamics parameters. Program 150 may utilize the location information in conjunction with vehicle dynamics data to provide contextual information such as weather, traffic density, and road type. In an embodiment, program 150 utilizes the vehicle dynamic data in conjunction with contextual information to retrieve further contextual information (e.g., regional events, accidents, etc.) from a plurality of internet accessible sources (e.g., news, social media, retail, etc.).

Program 150 captures driver physiological parameters (step 204). Physiological data contains any measurement of health of a driver including, but is not limited to, electrodermal response, glucose levels, breathing rate, heart rate, electromyography (EMG) feedback, electroencephalography feedback, galvanic skin response, blood pressure, pupil dilation, eye pressure, and body temperature. In an embodiment, physiological data includes associated health states such as stress, attention, fatigue, sleepiness, distraction, etc. Physiological data can be captured, monitored, derived, logged and stored from a plurality of sensors included within sensors 112 (e.g., heart monitor, glucose monitor, facial landmark recognition, etc.), as detailed in the description of sensors 112. In another embodiment, program 150 utilizes wearable computing devices (e.g., smartwatch, fitness tracker, etc.) to monitor the biometrics of the user in addition to the forces (e.g., g-forces) exerted on the user. For example, while driving a vehicle, program 150 detects and records a heartrate of the user elevated to 150 beats per minute (BPM) and perspiration increased 60% during a period of the trip. In this example, program 150 associates the elevated heartrate to a vehicle dynamics event such as excessive speed, rapid braking. Also, program 150 associates the physiological readings with contextual information such as increased traffic, drastic weather, and rough terrain (e.g., road type). In a further embodiment, program 150 may associate physiological data with location information (e.g., GPS coordinates) in addition to driving dynamic data. For example, a user, while driving, has a sudden rise in breathing rates due to increased elevation. In this example, program 150 distinguishes said variation in breathing rate from a variation caused by a vehicle dynamics event.

Program 150 trains the models (step 206). Program 150 retrieves a plurality of vehicle dynamics data and physiological data contained within one or more computing devices and database 122. In an embodiment, program 150 retrieves all historical data related to a user, including one or more time steps of behavioral parameters (e.g., including vehicle dynamics), health states (e.g., including physiological data), and creates one or more subsets of all historical data contained within database 122. In various embodiments, database 122 contains stored, inferred, or derived drive behavior parameters such as aggressiveness, average reaction time, smoothness (e.g., g-force, turn radii, etc.), etc. In an embodiment, database 122 contains user historical vehicle dynamics data such as vehicle parameters driver parameters, past trips, deviations, incidents (e.g., accidents, driving events, errors, etc.), and associated actions (e.g., remedial, corrective, informative, notifications, etc.).

Program 150 then partitions the recorded and retrieved vehicle dynamics and physiological data into a plurality of training, testing, and validation sets. In an embodiment, program 150 partitions the retrieved vehicle dynamics and physiological data into a plurality of separate sets. In an alternative embodiment, program 150 combines the retrieved vehicle dynamics and physiological data into a plurality of combined sets consisting of time stepped data where each time step has associated physiological, health states, vehicle dynamics data, contextual information, and driver behavior parameters. In this embodiments, associated information can be set as labels. Program 150 may vectorize the partitioned sets. In an embodiment, program 150 utilizes one-of-c coding to recode categorical data into a vectorized form. For example, when vectorizing an example feature set categorical (e.g., traffic conditions, weather, health states, etc.) consisting of [heavy rain, light rain, sunny], program 150 encodes the corresponding weather feature set into [[1,0,0], [0,1,0], [0,0,1]]. In another embodiment, program 150 utilizes featuring scaling techniques (e.g., rescaling, mean normalization, etc.) to vectorize and normalize numerical feature sets.

Program 150 can utilize supervised training techniques to determine the difference between a prediction and a target (i.e., the error), and back-propagate the difference through the layers such that one or more models contained within models 152 "learn." For example, program 150 utilizes stochastic gradient algorithms to implement backpropagation. Said algorithm may utilize the following function as the loss function, $-\log p_\theta(x^*_{t+1}|x_1, x_2, \ldots, x_t)$, where $x^*_{t+1}$ is the true symbol observed in the training data at the corresponding time step and where $\theta$ denotes the parameters of the model. Program 150 may adjust the learning rate in order to adjust cross-entropy cost, allowing program 150 to increase or decrease the adaptability of related cells and layers.

In various embodiments, program 150 creates, maintains, and utilizes multiple models, each specific to an intended relationship or correlation. In this embodiment, program 150 trains and stores one or more models inputting physiological data and outputting a plurality of health states associated with a driver. In an additional embodiment, program 150 utilizes maintained physical models that accept vehicle dynamic data as an input and output a plurality of driver behavior parameters. In various embodiments, program 150 maintains one or more recurrent neural networks trained utilizing continuous vehicle dynamics data (e.g., input) and when fed with subsequent vehicle dynamics data, outputs a driving behavioral parameter such as an aggressiveness rating. In an embodiment, program 150 utilizes unsupervised training methods to generate vehicle dynamics or driving behavioral parameters when continuous data is unavailable. In an embodiment, program 150 trains a plurality of models contained within models 152 with a plurality of feature vectors originating from and physiological data (e.g., time series of physiological parameters of a driver), and associated health states (e.g., time series of health state parameters of a driver).

Program 150 generates a risk assessment (step 208). Responsive to program 150 monitoring and processing vehicle dynamics data and physiological data (e.g., current operating information) provided by one or more computing devices, program 150 extracts, analyzes, and decomposes the information contained in said data, as discussed in steps 202 and 204. Program 150 utilizes one or more current (e.g., temporally relevant) time steps of data, captured by a driver driving or managing one or more vehicles by a plurality of active sensors, sensors 112, to input current vehicle and driver operating parameters into one or more trained models, as described in step 206, and output a risk assessment (e.g., score). For example, temporally relevant timesteps may include timesteps or predictions occurring in the next/last 5 minutes. In an embodiment, if there is missing data or a gap in continuous data (e.g., due to a faulty sensor, corrupted data, etc.), then program 150 utilizes linear regression (e.g., single or multiple) or unsupervised learning models to predict the missing values based on available data and historical values. In this embodiment, program 150 inputs the predicted values into one or more models contained within models 152.

Program 150 may input historical vehicle dynamics data (e.g., time series of vehicle dynamics data) and current (e.g., within 1 minute) vehicle dynamics data into one or more physical models utilized derive driving behavioral parameters. In an embodiment, program 150 inputs associated contextual information (e.g., time series of contextual data) and one or more physical model outputs into a behavior parameter learner (e.g., model, estimator, etc.) to derive driving behavioral parameters. In various embodiments, program 150 inputs the previously outputted driving behavioral parameters into a physiological-behavioral model learner and mapping model, allowing program 150 to learn one or more relationships (e.g., correlations, statistical significance, etc.) between driving behavioral parameters and physiological (e.g., health states) of a driver. In another embodiment, program 150 inputs health state parameters into trained physiological models, allowing program 150 to derive or associated physiological parameters from health state parameters. In an alternative embodiment, program 150 may derive physiological parameters or states to derive health state parameters.

In an embodiment, program 150 creates stacked models that receive the outputs of one or more physiological-health state models and one or more vehicle-dynamics-driving behavior models as inputs into a generalized risk assessment model (e.g., machine learning, recurrent neural network, etc.). In this embodiment, program 150 utilizes the aforementioned risk assessment model outputs a risk assessment score or categorization. In various embodiments, risk assessment scores represent a probability of an imminent accident (e.g., within a specified amount of time). In other embodiments, risk assessment scores represent a level of risk as would be defined in relation to an actual or insurance perspective. In other embodiments, risk assessment scores represent a likelihood that a driver induced error occurs. In an embodiment, program 150 creates a nonlinear mapping based on classic learning techniques (e.g., Bayesian inferences, deep learning, etc.) that factor context in the output. In another embodiment, models 152 contains a model that has two inputs (vehicle dynamics data and physiological data) and the output is a risk assessment. In this embodiment, associated health states and behavioral parameters are calculated and assessed in one or more hidden layers contained in the model.

In an embodiment, program 150 utilizes any combination of trained models (e.g., RNNs) to identify risky behavior within current operating parameters (e.g., vehicle dynamics/physiological sets). In a further embodiment, program 150 scores (e.g., weights) the outputs of parameter models to predict anticipated behaviors, physiological states, and associated risk factors. In an embodiment, program 150 processes, vectorizes, and feeds the monitored data into the aforementioned models within models 152 (e.g., risk assessment model). In this embodiment, models 152 outputs one or more sets of probabilities denoting the likelihood of risky behavior, an accident or major driving events. In another embodiment, program 150 utilizes the output generated by one or more calculations from models 152 to generate a risk assessment based on models trained with historical data. In a further embodiment, program 150 weighs each of the aforementioned results in proportion to the degree of risk confidence associated with each model.

In various embodiments, program 150 utilizes a predefined risk threshold. In this embodiment, if program 150 determines that an output (e.g., probability, etc.) is less than the risk threshold, then program 150 associates the monitored and capture data as safe or not risky. In yet another embodiment, the risk assessment is an aggregation of the described scores and ratings with distinct weights for any combination of variables, features, components, etc. In an embodiment, utilizing the output of models 152, program 150 determines whether the probability associated with the proposed solution is sufficient for an identified problem set. Program 150 utilizes models 152 to calculate and assigns weights to the various components of an operating vehicle to determine the likelihood (e.g., estimate of a measure or risk associated with the current context and health states and or driving behavior parameters) of an accident or driving event. The likelihood or probability is represented as a numerical percentage. In an embodiment, program 150 removes lower order parameters (e.g., vehicle dynamics and physiological parameters) after higher order parameters (e.g., behavioral parameters) or a risk assessment has been generated.

Program 150 sends an action (step 210). Responsive to a generation of a risk assessment (e.g., risk score), as detailed in step 208, program 150 sends or initiates a plurality of actions dependent on the risk assessment. In various embodiments, the action taken is either a corrective action and/or a remedial action. Corrective actions may include details about the recorded parameters, information, and data (e.g., vehicle dynamics and physiological). For example, if a vehicle or user is flagged with a specific risk assessment (e.g., probability (e.g., percentage) of occurrence of an accident, etc.), assessed risky for driving too close combined with driver poor reaction time, then program 150 sends a corrective notification instructing the driver to place more distance between the vehicles. In various embodiments, program 150 sends associated vehicle dynamics and physiological parameters to a plurality of entities and devices such as insurance companies, fleet coordinators, warnings systems contained within the vehicle or within a plurality of computing devices (e.g., mobile phone, fitness tracker, smart watch, in-dash devices, windshield displays, etc.). In some embodiments, program 150 may transmit the corrective notification to computing device 110 using a plurality of transmission methods including, but not limited to, short message service (SMS), email, push notification, automated phone call, text-to-speech, etc. For example, a driver receives a push notification on computing device 110 after being assessed a high risk for an accident. In one embodiment, program 150 may utilize text-to-speech methods to provide auditory instructions to mitigate or reduce risk to the driver. In another embodiment, program 150 sends a warning or notification to an advanced driver-assistance systems (ADAS) contained within the vehicle. In various embodiments, program 150 sends a warning, notifications, or instructions to the driver suggesting or scheduling a break stop, driver changeover, or any number of corrective actions.

In other embodiments, program 150 sends a remedial action if the driver ignores the corrective action and/or the driver is grossly at risk of an accident or major driving event. In an embodiment, a remedial action may be a generalized action used for all high-risk events. For example, after a series of high-risk notifications, program 150 prevents the driver from operating the vehicle after the vehicle is safely parked. For example, a trucker exceeding a risk threshold may be prevented from operating the vehicle until an authoritative entity approves or if program 150 determines that it is safe (e.g., low risk) to operate the vehicle. In an alternative embodiment, remedial actions may be a particular action for specific offenses. For example, numerous speeding related risk assessments may generate a specific remedial action, such as incentive schemes, adjusting of insurance policies and premiums (e.g., continuous updates to pricing policy (e.g., dynamic pricing), claims support, etc.) or revocation of a permit. In an embodiment, program 150 utilizes the following to determine the cost of an insurance policy as a function of real-time and historical data:

$$P\{X(t) \le x\} = \sum_{n=0}^{\infty} P(N(t)=n) F^{*n}(x) \quad (2)$$

With respect to equation (2), $F_i(x)=P(X_i \le x)$ and $F^{*n}(X) = \int_0^x F^{*(n-1)}(x-s) dF_1(s)$. Contrastingly, numerous following distance related high-risk assessments may generate a different remedial action, such as a citation or fine. In an embodiment, remedial actions are based upon the severity or amount of risk (e.g., risk score). In another embodiment, program 150 utilizes the following equation to determine individualist action:

$$X(t) = \sum_{i=1}^{n} X_i \quad (3)$$

With respect to equation (3), $F_i(x)=P(X_i \le x)$, where $X_i$ depends on real time and historical data of a driver and x is the fixed cost (e.g., percentage of parameter deviation). Said equation may control a mitigation action (e.g., rerouting, adjusted acceleration, etc.).

Still referring to step 210, in another embodiment, program 150 may send a remedial notification to the service operator of the driver. The service operator may be any company/entity that provides ride share, taxi, shipping, and/or transportation services. In addition, program 150 may also send a notification and/or report to a governmental regulatory body and/or law enforcement department. For example, if the driver is a taxi driver, program 150 sends a notification/report to the regional transportation authority. In some scenarios, the notification may include the name and ID of the driver, dynamic dynamics data (e.g., timestamp, parameter ID, deviation conditions, weather conditions, etc.). In another scenario, the user may set a threshold to determine which remedial action should take initiated. For example, after the driver exceeds a risk threshold, the user sets a remedial action of automatically terminating a ride share or taxi trip.

Program 150 may control one or more vehicles based on one or more generated risk assessments. In an embodiment, program 150 utilizes the generated risk assessments to determine a level of control of one or more vehicles. In this embodiment, program 150 may utilize any combination of the following level of controls: no automation; driver assistance, vehicle can control either steering or speed autonomously in specific circumstances to assist the driver; partial automation, vehicle can control both steering and speed autonomously in specific circumstances to assist the driver; conditional automation, vehicle can control both steering and speed autonomously under normal environmental conditions, but requires driver oversight; high automation, vehicle can complete a travel autonomously under normal environmental conditions, not requiring driver oversight; full autonomy, vehicle can complete a travel autonomously in any environmental conditions.

Mitigation actions may include modifying one or more driving or operating parameters of a vehicle, rerouting a vehicle, restricting one or more driving or operating parameters of a vehicle (e.g., limiting acceleration, etc.), or any of that actions described below. In another embodiment, program 150 may set governors or restrictions on a plurality of performance options and operating parameters of the vehicle, preventing the driver from certain actions determined to increase driver or vehicle risk. For example, if program 150 may restrict a vehicle to a maximum speed of 45 mph, preventing the driver from exceeding the maximum speed. Alternatively, program 150 may adjust the performance parameters of a vehicle to mimic a low risk driver (e.g., vehicle dynamics parameters that are determined to be low risk). For example, program 150 adjusts the drive-by-wire throttle of the vehicle to prevent a driver from exceeding an acceleration user parameter. In yet another embodiment, program 150 may utilize user parameters to adjust performance parameters and driving patterns for autonomous vehicles. For example, program 150 may adjust a plurality of vehicle options and controls such as performance, maneuvering, turning options, following distance based on a generated risk score. In this example, program 150 adjusts said parameters to minimize the probability of a vehicle, user, and driver incident based on inferences determined by a plurality of models fed with vehicle and physiological data and parameters. In various embodiments, program 150 fully controls one or more autonomous vehicles based on one or more risk assessments. For example, program 150 determines that a user is at risk of a major collision due to low attentiveness. In this example, program 150 fully controls the vehicle of the user and safely transports the vehicle. In another example, program 150 may determine that a near vehicle is at risk of colliding with a plurality of vehicles. In this example, program 150 controls the plurality of vehicles in order to avoid the risky vehicle.

Figure 3A:
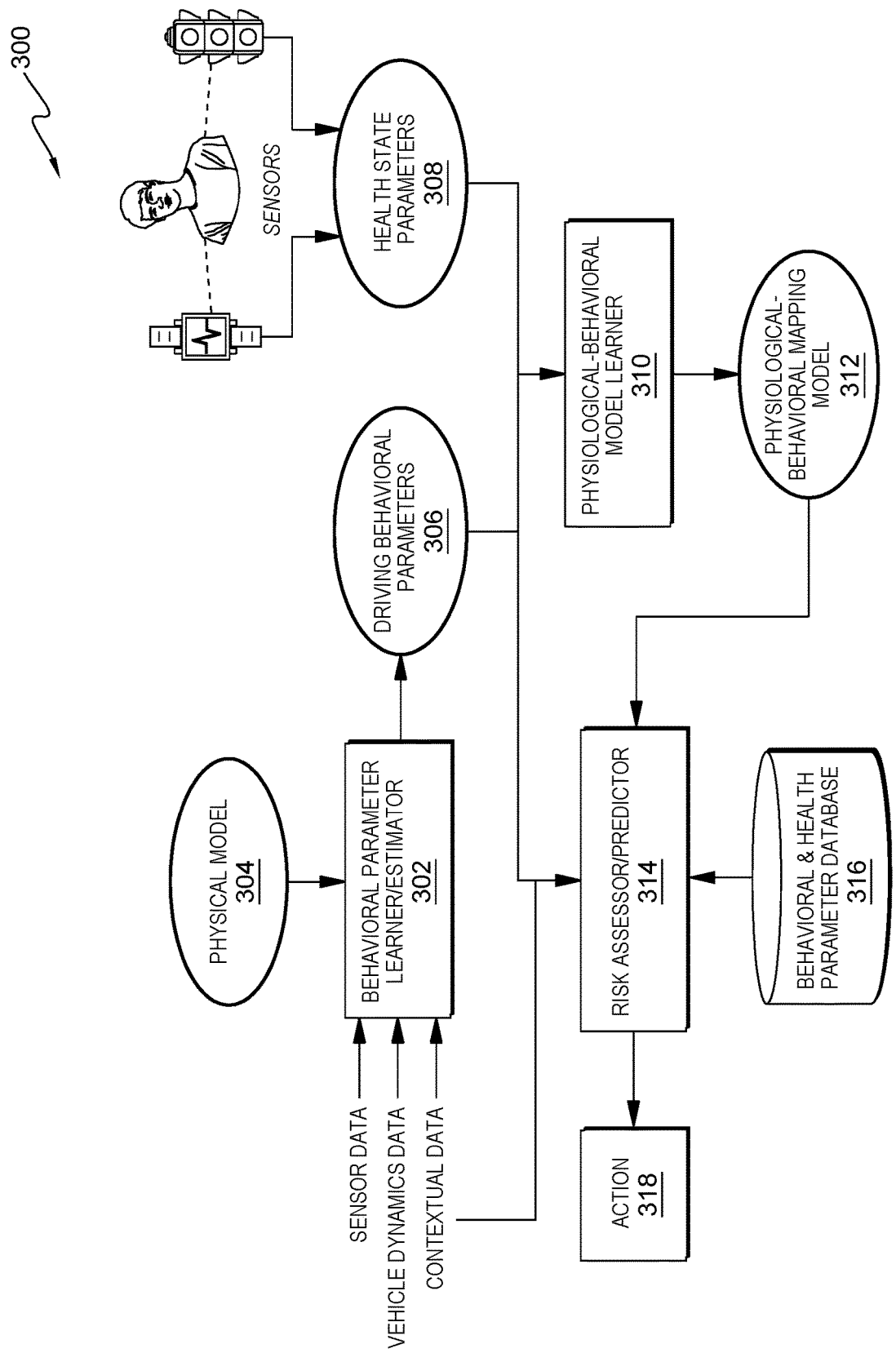
FIG. 3A illustrates an example embodiment of the operational steps of a program within the data processing environment of FIG. 1, in accordance with an embodiment of the present invention.

FIG. 3A depicts example 300, illustrative of an embodiment of the steps in flowchart 200. FIG. 3A contains behavioral parameter learner/estimator 302, learns and estimates behavioral parameters using physical behavioral models and input data; physical model 304, characterizes behavior of a driver based on vehicle dynamics; driving behavioral parameters 306, characterizes a driving behavior of a driver; health state parameters 308, characterizing a health condition of a driver; physiological behavioral model learner 310 and physiological behavioral mapping model 312, learn the correlation between behavioral and physiological parameters, infer the physiological parameters from behavioral parameters, and predict behavioral parameters based on physiological parameters; risk assessor/predictor 314, compares learned behavioral/physiological parameters to individual (e.g., specific to a user or driver) or collective (e.g., specific to multiple users, drivers, communities, or populations) distributions of behavioral/physiological parameters for the considered context and assess the driving risk; behavioral & health parameter database 316, database containing physiological data and health state data; action 318, initiates a warning, mitigation, or feedback action. In this embodiment, a mitigation action is triggered if there is a deviation from individual or collective distribution of observed behavioural and physiological parameters.

Figure 3B:
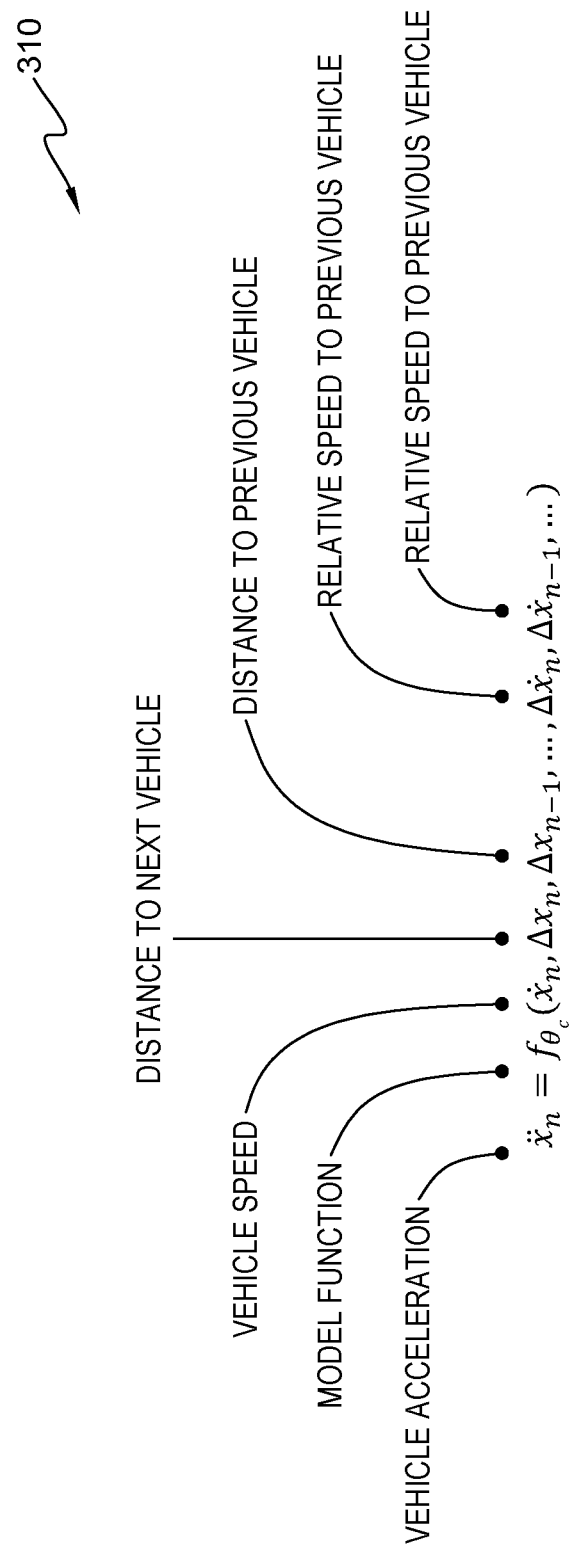
FIG. 3B illustrates an example of a driver behavior parameters physical model, in accordance with an embodiment of the present invention.

FIG. 3B depicts example physical model 320. With respect FIG. 3B $\theta_c$ is the vector of behavioral parameters (lane change aggressiveness, politeness factor, maximum speed, maximum acceleration, comfortable deceleration, reaction time, safe time headway, etc.), associated with the driver in a given context c (e.g., time step). Additional discrete sets of contexts (e.g., wet, dry, heavy traffic, etc.) are applied.

Figure 4:
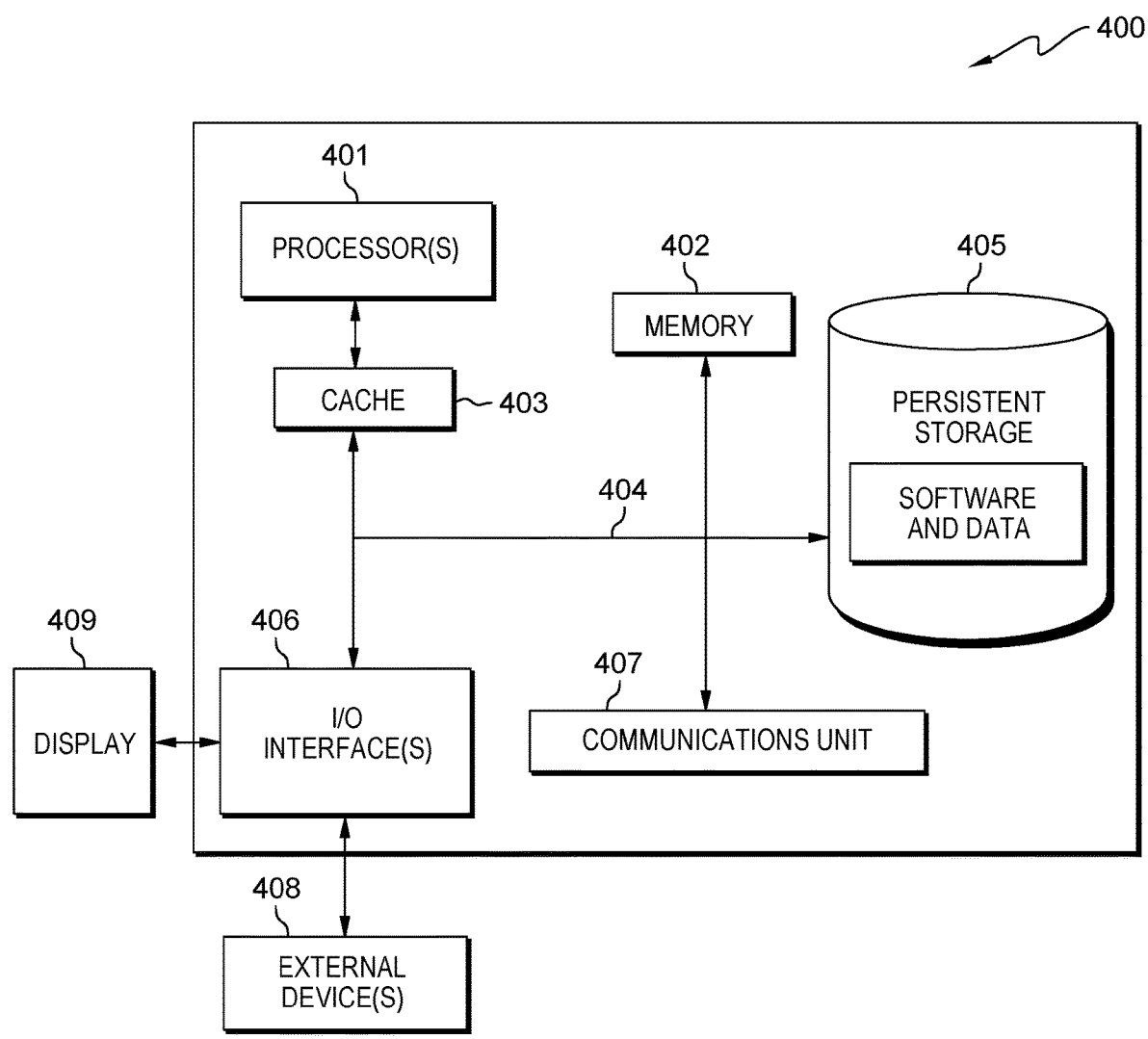
FIG. 4 is a block diagram of components of computing device and server computer, in accordance with an embodiment of the present invention.

FIG. 4 depicts a block diagram of components of computing device 110 and server computer 120 in accordance with an illustrative embodiment of the present invention. It should be appreciated that FIG. 4 provides only an illustration of one implementation and does not imply any limitations with regard to the environments in which different embodiments may be implemented. Many modifications to the depicted environment may be made.

Computing device 110 and server computer 120 includes communications fabric 404, which provides communications between cache 403, memory 402, persistent storage 405, communications unit 407, and input/output (I/O) interface(s) 406. Communications fabric 404 can be implemented with any architecture designed for passing data and/or control information between processors (such as microprocessors, communications, and network processors, etc.), system memory, peripheral devices, and any other hardware components within a system. For example, communications fabric 404 can be implemented with one or more buses or a crossbar switch.

Memory 402 and persistent storage 405 are computer readable storage media. In this embodiment, memory 402 includes random access memory (RAM). In general, memory 402 can include any suitable volatile or non-volatile computer readable storage media. Cache 403 is a fast memory that enhances the performance of computer processor(s) 401 by holding recently accessed data, and data near accessed data, from memory 402.

Program 150 may be stored in persistent storage 405 and in memory 402 for execution by one or more of the respective computer processor(s) 401 via cache 403. In an embodiment, persistent storage 405 includes a magnetic hard disk drive. Alternatively, or in addition to a magnetic hard disk drive, persistent storage 405 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 405 may also be removable. For example, a removable hard drive may be used for persistent storage 405. Other examples include optical and magnetic disks, thumb drives, and smart cards that are inserted into a drive for transfer onto another computer readable storage medium that is also part of persistent storage 405.

Communications unit 407, in these examples, provides for communications with other data processing systems or devices. In these examples, communications unit 407 includes one or more network interface cards. Communications unit 407 may provide communications through the use of either or both physical and wireless communications links. Program 150 may be downloaded to persistent storage 405 through communications unit 407.

I/O interface(s) 406 allows for input and output of data with other devices that may be connected, respectively, to computing device 110 and server computer 120. For example, I/O interface(s) 406 may provide a connection to external device(s) 408, such as a keyboard, a keypad, a touch screen, and/or some other suitable input device. External devices 408 can also include portable computer readable storage media such as, for example, thumb drives, portable optical or magnetic disks, and memory cards. Software and data used to practice embodiments of the present invention, e.g., program 150, can be stored on such portable computer readable storage media and can be loaded onto persistent storage 405 via I/O interface(s) 406. I/O interface(s) 406 also connect to a display 409.

Display 409 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, conventional procedural programming languages, such as the "C" programming language or similar programming languages, and quantum programming languages such as the "Q" programming language, Q#, quantum computation language (QCL) or similar programming languages, low-level programming languages, such as the assembly language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method comprising:
capturing, by one or more computer processors, one or more vehicle motion parameters;
capturing, by one or more computer processors, one or more physiological parameters;
identifying, by one or more computer processors, contextual data associated with the one or more captured vehicle motion parameters and the one or more captured physiological parameters;
predicting, by one or more computer processors, one or more driving behavior parameters by utilizing one or more physical models fed with the one or more vehicle motion parameters and the identified contextual data;
predicting, by one or more computer processors, one or more driver health parameters by utilizing a model trained with the one or more captured physiological parameters and the identified contextual data; and
generating, by one or more computer processors, a risk assessment based on the one or more predicted driving behavior parameters and the one or more predicted driver health parameters.

2. The method of claim 1, wherein generating the risk assessment based on the one or more predicted driving behavior parameters and the one or more predicted driver health parameters comprises:
training, by one or more computer processors, a risk assessor utilizing one or more historically predicted driving behavior parameters and one or more historically predicted driver health parameters.

3. The method of claim 1, further comprising:
responsive to the generated risk assessment exceeding a risk threshold, initiating, by one or more computer processors, one or more mitigation actions.

4. The method of claim 3, wherein the one or more mitigation actions comprise modifying, by one or more computer processors, driving parameters of a vehicle.

5. The method of claim 1, wherein physiological parameters are selected from the group consisting of: electrodermal response, glucose level, breathing rate, heart rate, electromyography feedback, electroencephalography feedback, galvanic skin response, blood pressure, pupil dilation, eye pressure, and body temperature.

6. The method of claim 1, wherein vehicle dynamic parameters are selected from the group consisting of: speed, acceleration, longitudinal and lateral distances to surrounding vehicles, orientation, coordinate acceleration, noise, vibration, shock, wobble, weight transfer, load transfer, yaw, roll, pitch, body roll, bump steer, and body flex.

7. The method of claim 1, wherein contextual data is selected from the group consisting of: weather, traffic status, road quality, speed limits, construction considerations, natural disasters, and regional events.

8. The method of claim 1, further comprising:
predicting, by one or more computer processors, one or more unavailable vehicle motion parameters and one or more unavailable driver physiological parameters utilizing linear regression.

9. The method of claim 1, further comprising:
adjusting, by one or more computer processors, one or more insurance policies, premiums, and revocations based on one or more generated risk assessments.

10. The method of claim 1, wherein generating the risk assessment based on the one or more predicted driving behavior parameters and the one or more predicted driver health parameters, comprises:
generating, by one or more computer processors, the risk assessment utilizing individualistic parameters.

11. The method of claim 1, generating, by one or more computer processors, a risk assessment based on the one or more predicted driving behavior parameters and the one or more predicted driver health parameters, comprises:
generating, by one or more computer processors, the risk assessment utilizing collective parameters.

12. A computer program product comprising:
one or more computer readable storage media and program instructions stored on the one or more computer readable storage media, the stored program instructions comprising:
program instructions to capture one or more vehicle motion parameters;
program instructions to capture one or more physiological parameters;
program instructions to identify contextual data associated with the one or more captured vehicle motion parameters and the one or more captured physiological parameters;
program instructions to predict one or more driving behavior parameters by utilizing one or more physical models fed with the one or more vehicle motion parameters and the identified contextual data;
program instructions to predict one or more driver health parameters by utilizing a model trained with the one or more captured physiological parameters and the identified contextual data; and
program instructions to generate a risk assessment based on the one or more predicted driving behavior parameters and the one or more predicted driver health parameters.

13. The computer program product of claim 12, wherein physiological parameters are selected from the group consisting of: electrodermal response, glucose level, breathing rate, heart rate, electromyography feedback, electroencephalography feedback, galvanic skin response, blood pressure, pupil dilation, eye pressure, and body temperature.

14. The computer program product of claim 12, wherein vehicle dynamic parameters are selected from the group consisting of: speed, acceleration, longitudinal and lateral distances to surrounding vehicles, orientation, coordinate acceleration, noise, vibration, shock, wobble, weight transfer, load transfer, yaw, roll, pitch, body roll, bump steer, and body flex.

15. The computer program product of claim 12, wherein contextual data is selected from the group consisting of: weather, traffic status, road quality, speed limits, construction considerations, natural disasters, and regional events.

16. The computer program product of claim 12, wherein the program instructions stored on the one or more computer readable storage media comprise:
program instructions to adjust one or more insurance policies, premiums, and revocations based on one or more generated risk assessments.

17. A computer system comprising:
one or more computer processors;
one or more computer readable storage media; and
program instructions stored on the computer readable storage media for execution by at least one of the one or more processors, the stored program instructions comprising:
program instructions to capture one or more vehicle motion parameters;
program instructions to capture one or more physiological parameters;
program instructions to identify contextual data associated with the one or more captured vehicle motion parameters and the one or more captured physiological parameters;
program instructions to predict one or more driving behavior parameters by utilizing one or more physical models fed with the one or more vehicle motion parameters and the identified contextual data;
program instructions to predict one or more driver health parameters by utilizing a model trained with the one or more captured physiological parameters and the identified contextual data; and
program instructions to generate a risk assessment based on the one or more predicted driving behavior parameters and the one or more predicted driver health parameters.

18. The computer system of claim 17, wherein physiological parameters are selected from the group consisting of: electrodermal response, glucose level, breathing rate, heart rate, electromyography feedback, electroencephalography feedback, galvanic skin response, blood pressure, pupil dilation, eye pressure, and body temperature.

19. The computer system of claim 17, wherein vehicle dynamic parameters are selected from the group consisting of: speed, acceleration, longitudinal and lateral distances to surrounding vehicles, orientation, coordinate acceleration, noise, vibration, shock, wobble, weight transfer, load transfer, yaw, roll, pitch, body roll, bump steer, and body flex.

20. The computer system of claim 17, wherein contextual data is selected from the group consisting of: weather, traffic status, road quality, speed limits, construction considerations, natural disasters, and regional events.

* * * * *